US00PP37660P2

(12) United States Plant Patent
Moseley

(10) Patent No.: US PP37,660 P2
(45) Date of Patent: Sep. 1, 2026

(54) ***LOBELIA* PLANT NAMED 'WILODABLU27'**

(50) Latin Name: *Lobelia hybrida*
Varietal Denomination: WILODABLU27

(71) Applicant: Adam Moseley, Kyle, TX (US)

(72) Inventor: Adam Moseley, Kyle, TX (US)

(73) Assignee: WINGEN, LLC, Mustang Ridge, TX (US)

( * ) Notice: Subject to any disclaimer, the term of this patent is extended or adjusted under 35 U.S.C. 154(b) by 0 days.

(21) Appl. No.: 19/401,278

(22) Filed: Nov. 25, 2025

(51) Int. Cl.
*A01H 5/02* (2018.01)
*A01H 6/26* (2018.01)

(52) U.S. Cl.
USPC ..... Plt./451

(58) Field of Classification Search
USPC ..... Plt./451
CPC ..... A01H 5/02; A01H 6/268; A01H 6/26
See application file for complete search history.

(56) References Cited

U.S. PATENT DOCUMENTS

PP35,501 P2 * 11/2023 Tashiro ..... A01H 6/268
Plt./451

* cited by examiner

*Primary Examiner* — June Hwu
(74) *Attorney, Agent, or Firm* — C. Anne Whealy

(57) ABSTRACT

A new and distinct cultivar of *Lobelia* plant named 'WILODABLU27', characterized by its upright to outwardly spreading and mounding to eventually trailing plant habit; vigorous and sturdy growth habit; freely branching habit; dense and bushy plant form; freely flowering habit; long flowering period; large deep violet blue-colored flowers with small white-colored centers; tolerance to high temperatures; and good container and garden performance.

2 Drawing Sheets

Figure 1:
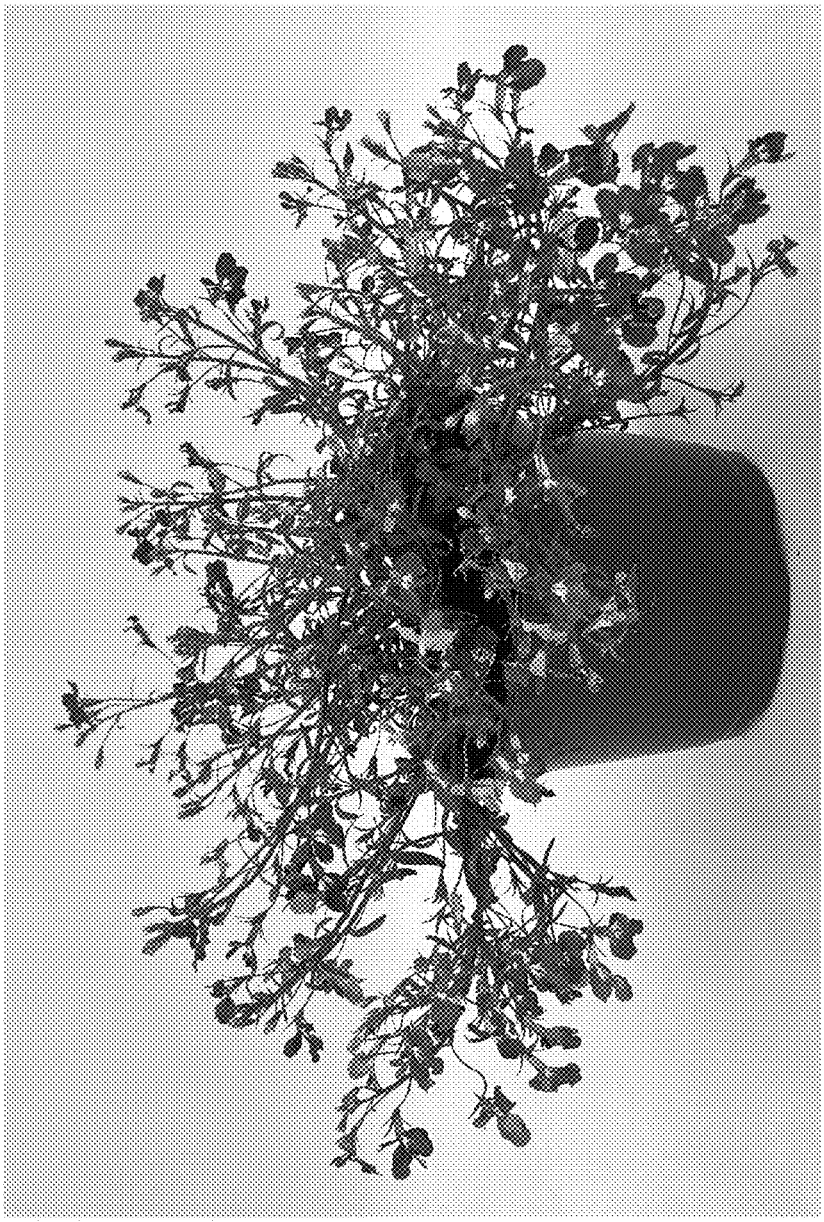

Botanical designation: *Lobelia hybrida.*
Cultivar denomination: 'WILODABLU27'.

BACKGROUND OF THE INVENTION

The present invention relates to a new and distinct cultivar of *Lobelia* plant, botanically known as *Lobelia hybrida* and hereinafter referred to by the name 'WILODABLU27'.

The new *Lobelia* plant is a product of a planned breeding program conducted by the Inventor in Alajuela, Costa Rica and Mustang Ridge, Texas. The objective of the breeding program is to create new mounding and freely-branching *Lobelia* plants with a long flowering period, high temperature tolerance and good container and garden performance.

The new *Lobelia* plant originated from a cross-pollination made by the Inventor in Alajuela, Costa Rica on Sep. 15, 2021 of a proprietary seedling selection of *Lobelia hybrida* identified as code number LOB-0565-02, not patented, as the female, or seed, parent with a proprietary seedling selection of *Lobelia hybrida* identified as code number LOB-0523-01, not patented, as the male, or pollen, parent. The new *Lobelia* plant was discovered and selected by the Inventor as a single flowering plant within the progeny of the stated cross-pollination in a controlled greenhouse environment in Mustang Ridge, Texas on Oct. 19, 2022.

Asexual reproduction of the *Lobelia* plant by vegetative terminal cuttings in Mustang Ridge, Texas since Nov. 1, 2022 has shown that the unique features of this new *Lobelia* plant are stable and reproduced true to type in successive generations.

SUMMARY OF THE INVENTION

Plants of the new *Lobelia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'WILODABLU27'. These characteristics in combination distinguish 'WILODABLU27' as a new and distinct *Lobelia* plant:

1. Upright to outwardly spreading and mounding to eventually trailing plant habit.
2. Vigorous and sturdy growth habit.
3. Freely branching habit; dense and bushy plant form.
4. Freely flowering habit.
5. Long flowering period.
6. Large deep violet blue-colored flowers with small white-colored centers.
7. Tolerant to high temperatures.
8. Good container and garden performance.

Plants of the new *Lobelia* differ primarily from plants of the female parent selection, in the following characteristics:

1. Plants of the new *Lobelia* are more vigorous than plants of the female parent selection.
2. Flowers of plants of the new *Lobelia* are deep violet blue in color with small white-colored centers whereas flowers of plants of the female parent selection are darker violet blue in color with larger white-colored centers.

Plants of the new *Lobelia* differ primarily from plants of the male parent selection in the following characteristics:

1. Growth habit of plants of the new *Lobelia* is denser than and not as open as growth habit of plants of the male parent selection.

2. Plants of the new *Lobelia* flower for a longer period of time than plants of the male parent selection.
3. Flowers of plants of the new *Lobelia* are deep violet blue in color with small white-colored centers whereas flowers of plants of the male parent selection are lighter violet blue in color with larger white-colored centers.
4. Plants of the new *Lobelia* are more tolerant to high temperatures than plants of the male parent selection.

Plants of the new *Lobelia* can be compared to plants of *Lobelia erinus* 'WNLOBLSB23', disclosed in U.S. Plant Pat. No. 35,592. In side-by-side comparisons, plants of the new *Lobelia* differ primarily from plants of 'WNLOBLSB23' in the following characteristics:

1. Leaves of plants of the new *Lobelia* are darker green and glossier than leaves of plants of 'WNLOBLSB23'.
2. Plants of the new *Lobelia* have larger flowers than plants of 'WNLOBLSB23'.
3. Flowers of plants of the new *Lobelia* are deep violet blue in color whereas flowers of plants of 'WNLOBLSB23' are bright purplish blue to light violet in color.

BRIEF DESCRIPTION OF THE PHOTOGRAPHS

The accompanying colored photographs illustrate the overall appearance of the new *Lobelia* plant showing the colors as true as it is reasonably possible to obtain in colored reproductions of this type. Colors in the photographs may differ slightly from the color values cited in the detailed botanical description which accurately describe the actual colors of the new *Lobelia* plant.

The photograph on the first sheet (FIG. 1) is a side perspective view of a typical flowering plant of 'WILODABLU27' grown in a container.

Figure 2:
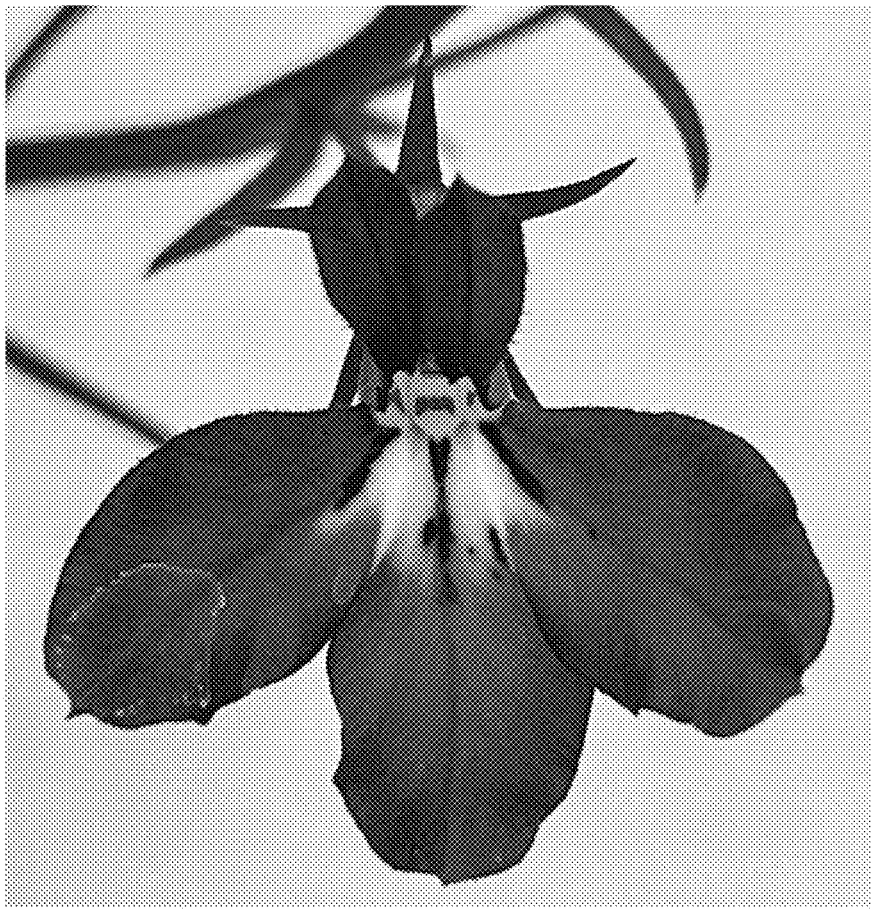

The photograph on the second sheet (FIG. 2) is a close-up view of typical flower of 'WILODABLU27'.

DETAILED BOTANICAL DESCRIPTION

The aforementioned photographs and following observations and measurements describe plants grown during the late summer to early autumn in 740-ml containers in a glass-covered greenhouse in Loudon, New Hampshire and under cultural practices typical of commercial *Lobelia* production. During the production of the plants, day temperatures ranged from 18° C. to 20° C. and night temperatures ranged from 16° C. to 18° C. Plants were pinched one time and were eight weeks from planting rooted young plants when the photographs and description were taken. In the following description, color references are made to The Royal Horticultural Society Colour Chart, 2015 Edition, except where general terms of ordinary dictionary significance are used.

Botanical classification: *Lobelia hybrida* 'WILODABLU27'.

Parentage:

*Female, or seed, parent*.—Proprietary seedling selection of *Lobelia hybrida* identified as code number LOB-0565-02, not patented.

*Male, or pollen, parent*.—Proprietary seedling selection of *Lobelia hybrida* identified as code number LOB-0523-01, not patented.

Propagation:

*Type cutting*.—Vegetative terminal cuttings.

*Time to initiate roots, summer*.—About seven to twelve days at ambient temperatures about 28° C.

*Time to initiate roots, winter*.—About 10 to 14 days at ambient temperatures about 20° C.

*Time to produce a rooted young plant, summer*.—About three to four weeks at ambient temperatures about 28° C.

*Time to produce a rooted young plant, winter*.—About four to five weeks at ambient temperatures about 20° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Upright to outwardly spreading and mounding to eventually trailing plant habit; freely branching habit with lateral branches developing at potentially every node; dense and bushy plant habit; vigorous and sturdy growth habit and rapid growth rate.

*Plant height*.—About 14 cm to 16 cm.

*Plant width*.—About 30 cm to 32 cm.

*Lateral branch description*.—Length: About 14 cm to 18 cm. Diameter: About 1.5 mm to 2 mm. Internode length: About 1 cm to 1.5 cm. Strength: Strong, flexible; wiry. Aspect: Upright to outwardly spreading to eventually trailing. Texture and luster: Smooth, glabrous; longitudinally ridged; glossy. Color: Close to 146A.

Leaf description:

*Arrangement*.—Alternate, simple; sessile.

*Length*.—About 2.25 cm to 2.5 cm.

*Width*.—About 5 mm.

*Shape*.—Linear.

*Apex*.—Acute to broadly acute.

*Base*.—Decurrent.

*Margin*.—Entire; not undulate.

*Texture and luster, upper and lower surfaces*.—Smooth, glabrous; semi-glossy.

*Venation pattern*.—Pinnate.

*Color*.—Developing and fully expanded leaves, upper surface: Close to 146A; venation, close to 146A. Developing and fully expanded leaves, upper surface: Close to 146A to 146B; venation, close to 146B.

Flower description:

*Flower arrangement, habit and shape*.—Single, flowers axillary or terminal; flowers face mostly outwardly; freely flowering habit with flowers potentially developing at every axil; flowers bilabiate with two small upper petals and three larger fused lower petals.

*Fragrance*.—None detected.

*Natural flowering season*.—Long flowering period, in New Hampshire, plants of the new *Lobelia* flower continuously from planting in the spring until frost in the autumn; early flowering habit, plants begin flowering about seven to eight weeks after planting rooted young plants.

*Flower longevity on the plant*.—Longevity of individual flowers is highly dependent on temperature, flowers typically last about seven to ten days on the plant; petals not persistent and sepals persistent.

*Flower height* (*vertical*).—About 1.75 cm.

*Flower width* (*horizontal*).—About 2.1 cm.

*Flower depth*.—About 1.25 cm.

*Flower throat diameter*.—About 2 mm.

*Flower tube length*.—About 9 mm.

*Flower tube diameter, proximally*.—About 2 mm.

*Flower buds*.—Length: About 1 cm. Diameter: About 3 mm. Shape: Clavate. Color, developing sepals: Close to 144A.

*Petals*.—Arrangement: Single whorl of five petals fused towards the base; two small upper petals and three larger fused lower petals. Upper petals: Lobe length, beyond throat: About 7 mm. Lobe width, beyond throat: About 3 mm. Shape: Obovate to oblanceolate. Apex: Cuspidate. Margin: Entire; with occasional ciliation; not undulate. Texture and luster, upper and lower surfaces: Smooth, glabrous; matte. Color: When opening, upper surface: Close to 94A. When opening, lower surface: Close to 94B. Fully opened, upper surface: Close to 94A; towards the throat, close to NN155D; throat, close to 94C to 94D; venation, similar to lamina colors; colors do not change with subsequent development. Fully opened, lower surface: Close to 94C; tube, close to 94C to 94D; venation, similar to lamina colors; colors do not change with subsequent development. Lower petals: Lobe length, beyond throat: About 1.2 cm. Lobe width, beyond throat: About 8 mm. Shape: Obovate to broadly elliptic. Apex: Obtuse and cuspidate. Margin: Entire; not undulate. Texture and luster, upper and lower surfaces: Smooth, glabrous; matte. Color: When opening, upper surface: Close to 94A. When opening, lower surface: Close to 94B. Fully opened, upper surface: Close to 94A; towards the throat, close to NN155D; throat, close to NN155D with chevrons, close to 93B, and nectar guides, close to 5A; venation, similar to lamina colors; colors do not change with subsequent development. Fully opened, lower surface: Close to 94C; tube, close to 94C to 94D; venation, similar to lamina colors; colors do not change with subsequent development.

*Sepals*.—Arrangement: Single whorl of five sepals, fused at the base; star-shaped calyx. Length: About 5 mm to 6 mm. Width: About 1 mm. Shape: Acicular. Apex: Acute. Margin: Entire; not undulate. Texture and luster, upper and lower surfaces: Smooth, glabrous; slightly glossy. Color, upper and lower surfaces: Close to 146A.

*Peduncles*.—Length: About 5 mm to 7 mm. Diameter: About 1 mm. Strength: Strong, flexible; wiry. Aspect: About 45° from the lateral branch axis. Texture and luster: Smooth, glabrous; slightly glossy. Color: Close to 146A.

*Reproductive organs*.—Stamens: To date, stamen development has not been observed on plants of the new *Lobelia*. Pistils: Quantity per flower: One. Pistil length: About 9 mm to 10 mm. Stigma shape: Globose. Stigma color: Close to N81A. Style color: Proximally, close to NN155A and distally, close to NN155A tinged with close to 94B to 94C. Ovary color: Close to 144A.

*Fruits and seeds*.—To date, fruit and seed development have not been observed on plants of the new *Lobelia*.

Pathogen & pest resistance: To date, plants of the new *Lobelia* have not been noted to be resistant to pathogens and pests common to *Lobelia* plants.

Garden performance: Plants of the new *Lobelia* have been observed to have good garden performance and to tolerate wind, rain and to be tolerant to high temperatures of about 40° C.

It is claimed:

1. A new and distinct *Lobelia* plant named 'WILODABLU27' as herein illustrated and described.

* * * * *